United States Patent
Tournier et al.

(10) Patent No.: US 6,217,849 B1
(45) Date of Patent: *Apr. 17, 2001

(54) LIPOSOME SUSPENSIONS AS BLOOD POOL IMAGING CONTRAST AGENTS

(75) Inventors: Hervé Tournier, Valleiry (FR); Bernard Lamy, Geneva (CH)

(73) Assignee: Bracco Research S.A., Carouge (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/882,351

(22) Filed: Jun. 25, 1997

Related U.S. Application Data (62) Continuation of application No. 08/605,976, filed on Feb. 23, 1996, now abandoned, which is a continuation-in-part of application No. 08/440,134, filed on May 12, 1995, now Pat. No. 5,626,832, which is a continuation of application No. 08/128,206, filed on Sep. 29, 1993, now Pat. No. 5,445,810, which is a continuation of application No. 07/302,690, filed as application No. PCT/EP88/00447 on May 16, 1989, now Pat. No. 5,312,615.

(30) Foreign Application Priority Data

Feb. 24, 1995 (EP) .................................................. 95810123

(51) Int. Cl.⁷ .......................... A61B 5/055; A61K 49/04
(52) U.S. Cl. ...................... 424/9.321; 424/9.36; 424/9.4; 424/9.45
(58) Field of Search ................................ 424/9.321, 9.4, 424/9.32, 9.51, 450, 9.3, 9.36, 9.44, 9.451

(56) References Cited

U.S. PATENT DOCUMENTS

| | | | | |
|---|---|---|---|---|
| 4,830,858 | * | 5/1989 | Payne et al. | 424/450 |
| 5,015,483 | * | 5/1991 | Haynes et al. | 426/73 |
| 5,550,263 | * | 8/1996 | Herslof et al. | 554/78 |
| 5,585,112 | * | 12/1996 | Unger et al. | 424/450 |
| 5,651,991 | * | 7/1997 | Sugiyama et al. | 424/502 |

FOREIGN PATENT DOCUMENTS

| | | |
|---|---|---|
| WO 88/04924 | 7/1988 | (WO) . |
| WO 88/09165 | 12/1988 | (WO) . |
| 8809165 * | 12/1988 | (WO) ............... A61K/9/50 |
| WO 92/10166 | 6/1992 | (WO) . |
| 9210166 * | 6/1992 | (WO) ............... A61K/9/127 |
| WO 95/26205 | 10/1995 | (WO) . |
| 9526205 * | 10/1995 | (WO) ............... A61K/49/04 |

OTHER PUBLICATIONS

*Biochimica et Biophysica Acta*, vol. 1103, No. 1, 1992; A. Gabizon et al: "The Role of Surface Charge and Hydrophilic Groups in Liposome Clearance in VIVO," pp. 94–100.

*Magnetic Resonance in Medicine*, vol. 13, No. 1, 1990; G. Bacic et al: "NMR and ERS Study of Liposome Delivery of MN2+ to Murine Liver," pp. 44–61.

*Proceedings of the National Academy of Sciences*, vol. 75, No. 9, 1978; F. Szoka et al: "Procedure For Preparation of Liposomes with a Large Internal Aqueous Space and High Capture by Reverse–Phase Evaporation," pp. 4196–4198.

* cited by examiner

Primary Examiner—Michael G. Hartley
(74) Attorney, Agent, or Firm—Nixon & Vanderhye (57) ABSTRACT

The present invention concerns injectable blood pool contrast agents for NMR and X-ray imaging purpose. These blood pool agents carry imaging contrast enhancers, e.g. paramagnetic or, respectively, radio-opaque compounds for imaging the circulation and/or circulation targeted organs. The blood pool agent compositions are formulated to protect the contrast agents from early removal by the reticuloendothelial (RES) system of the liver and the spleen, so that they stay in the circulation long enough to provide good images of the blood vessels and blood perfused organs. X-ray and NMR imaging of the circulation and of targeted organs can strongly assist in diagnosing possible ailments in human and animal patients.

18 Claims, 2 Drawing Sheets

LIPOSOME SUSPENSIONS AS BLOOD POOL IMAGING CONTRAST AGENTS

CROSS-REFERENCE TO RELATED APPLICATIONS

This application is a continuation of application Ser. No. 08/605,976, filed Feb. 23, 1996, now abandoned, which is a continuation-in-part of earlier application Ser. No. 08/440,134 filed May 12, 1995, now U.S. Pat. No. 5,626,832 which is a continuation of Ser. No. 08/128,206 filed Sep. 29, 1993 now U.S. Pat. No. 5,445,810 which is a continuation of Ser. No. 07/302,690 filed Jan. 19, 1989 now U.S. Pat. No. 5,312,615 which is a 35 USC 371 of PCT/EP88/00447 filed May 16, 1988.

TECHNICAL FIELD

The present invention concerns injectable NMR and X-ray blood pool contrast agents comprising aqueous suspensions of liposomes carrying imaging contrast enhancers, e.g. paramagnetic or, respectively, radio-opaque compounds for imaging the circulation and/or circulation targeted organs. The compositions are formulated to protect the contrast agents from early removal by the reticulo-endothelial (RES) system of the liver and the spleen, so that they stay in the circulation long enough for imaging the blood vessels and blood perfused organs. X-ray and NMR imaging of the circulation and of targeted organs can strongly assist in diagnosing possible ailments in human and animal patients.

BACKGROUND ART

Until now, substances suitable as imaging contrast agents in injectable compositions for blood-pool investigations have been mostly NMR responsive solid mineral and organic particles or water-soluble polymers. The particles can comprise ferromagnetic or superparamagnetic materials as well as paramagnetic species bonded to polymeric carriers. In order to make them sufficiently long lasting for imaging the circulation, the particles should be protected against premature removal from the bloodstream.

Normally, the useful life of particles injected in the circulation is short because of rapid physiological removal therefrom due to opsonization followed by phagocytosis. The opsonization process involves the coating of the particles by an antigen protein, opsonin, recognisable by macrophages. Then, in a second stage, opsonization is followed, by the phagocytosis and metabolization of the coated (opsonized) particles by the Kupffer cells of the liver and spleen. Hence, although unprotected particles are suitable for imaging of the liver and the spleen, their free life in the blood is too short for blood-pool imaging.

The protection of particles against early removal from the circulation is discussed in many documents and significant enhancement of their useful life in the blood has been achieved by coating magnetite particles with a coating which includes amphiphilic substances, for example ethyleneoxide-propyleneoxide block copolymers (see for instance WO-A-94/04197, Sintetica).

The use of dispersions of microvesicles containing concentrated solutions of iodinated or paramagnetic species encapsulated in the vesicles e.g. liposomes as carriers of X-ray opacifiers or NMR contrast agents has been proposed. Thus, EP-A-0 314 764 (Dibra) discloses injectable aqueous suspensions of liposomal vesicles carrying encapsulated at least one iodinated organic compound opaque to X-rays which are useful as contrast agents for X-ray imaging of liver and spleen. The liposomes have a mean size between 0.15 and 3 $\mu$m and the ratio of the weight of the iodine encapsulated in the liposomes to the weight of the liposome forming lipids (I/L) is from 1.5 to 6 g/g. The liposome suspensions as carriers of opacifying compounds have been proposed due to their relative biocompatibility and ease of preparation.

Proposals to incorporate opacifiying agents into the liposome membranes have also been made (E. Unger et al., Liposome bearing membrane-bound complexes of manganese as magnetic resonance contrast agents, Proceedings of the Contrast Media Research Symposium, San Antonio Tex. Oct. 3–8, 1993, S168). However, most liposomes are subject to rapid removal from the circulation by the liver and the spleen and, although this property may be advantageous for imaging of these organs it is undesirable when blood pool imaging is contemplated. This since for blood pool imaging the concentrations of opacifying compounds in the blood should be kept at a relatively high level for extended periods of time.

To prolong the life of liposomes vesicles in the blood, different remedies have been proposed. Coating liposomes with copolymers containing hydrophilic and hydrophobic segments has been proposed in, for instance, J. Pharmacy & Pharmacol. 39 (1987), 52P, while incorporation of protective substances in the vesicle forming lipids has been proposed in EP-A-0 354 855 (Terumo) and in WO-A-91/05545 (Liposome Technology). Along the latter line of approach, "stealth factors", for instance, covalently modified lipids, i.e. lipids carrying grafted thereon externally extending polyethylene glycol (PEG) or polyoxyethylene-polyoxypropylene segments. Also, the incorporation, as "stealth" factors, to the vesicle forming lipids of products such as palmitoylglucuronic acid (PGlcUA) has been reported to improve the half-life of liposomes in the blood (see Naoto Oku et al. in Biochimica et Biophysica Acta 1126 (1992), 255–260).

EP-A-0 354 855 (Terumo) discloses use of agents for inhibiting adsorption of protein on the liposome surface comprising a hydrophobic moiety at one end and a hydrophilic macromolecular chain moiety on the other end. The preferred hydrophobic moieties are alcoholic radicals of long chain aliphatic alcohol, a sterol, a polyoxypropylene alkyl or a glycerin fatty acid ester and phospholipids while prefered hydrophilic moieties are polyethylene glycols (PEG). Non-ionic surface active agents in which PEG and an alcoholic radical of the hydrophobic moiety are bound by ether bond or PEG-bound phospholipids are particularly preferred. Upon formation the agent is admixed with liposome forming phospholipids to produce "stealth" liposomes.

The lifetime of liposomes in the blood may be significantly prolonged by making the vesicles very small, i.e. making them less size-recognisable by opsonin; this approach has been disclosed in WO-A-88/04924 and EP-A-0 442 962.

WO-A-88/04924 discloses liposome compositions containing an entrapped pharmaceutical agent in which the liposomes are predominantly between 0.07 and 0.5 $\mu$m in size, have at least 50% mole of membrane-rigidifying lipid such as sphingomyelin or neutral phospholipids and between 5–20% mole of ganglioside $GM_1$, saturated phosphatidyl inositol or galactocerebroside sulfate ester. From the disclosure (Examples 8 and 9) it follows that liposomes made with negatively charged phospholipids in which phosphatidyl moiety is linked to glycerol are not very useful for blood pool applications as the same are relatively quickly recognised by RES.

In EP-A-0 442 962 liposomes of 50 nm or less are proposed for transporting through the circulation minute amounts of drugs to selected areas in the body. The trouble with very small vesicles is that their entrapment capacity becomes very low and such small vesicles are not readily compatible with the amounts of contrast media required for imaging the blood-pool with paramagnetic or X-ray compounds. Thus, under the conditions disclosed it would be necessary to inject to live subjects liposome suspensions containing more than 100 mg of lipids/ml which is undesirable for reasons of cost, potential toxicity and very high viscosity. The use of tiny liposome vesicles of the kind proposed in EP-A-0 442 962 for the delivery of drugs (in the order of 50 nm or less) are therefore unpractical for blood-pool imaging. Much the same applies to the proposals of Gabizon et al. in Biochim. et Biophys. Acta 1103 (1992) 94–100 and I. A. J. M. Bakker-Woudenberg et al. ibid. 318–326 directed to liposomes with an average size between 0.07 μm and 0.1 μm and prolonged residence times in the blood.

From the recent publications of M. C. Woodle et al., Journal of Drug Targeting 2 (1994) 397–403 and I. A. J. M. Bakker-Woudenberg et al., ibid. 363–371, it follows that in view of a relatively rapid removal of even those very small liposomes, the presence of the recognised stealth factors is absolutely necessary if these liposomes are to be effective in transporting various targeted drugs. This then presents further problems as the production of liposomes with the "stealth factors" is rather cumbersome. In addition, the "stealth factored" liposomes are known to have very low entrapment capacity and while such liposomes may be suitable to carry specific drugs, and therefore useful in therapy, they are almost useless in imaging.

Hence, the problem of use of standard or unmodified liposomes i.e. liposomes which can carry sufficient amount of opacifier and remain in the blood circulation sufficently long to enable X-ray and NMR imaging remains unresolved. It is generally believed that, in addition to be able to supply sufficent amount of opacifier, for good blood pool imaging the contrast agent should upon administration remain in the circulation between 1 and 2 hours. Thereafter the blood pool contrast agent should be eliminated from the body as quickly as possible. Use of liposomes which would satisfy these criteria is desirable as liposome production techniques are well known; their use in medicine and diagnostic preparations is wide spread; their effects in the living body are reasonably well understood. Hence their use for blood pool imaging or the manufacture of blood pool agents of "stealth" liposomes without "stealth factors" would provide a number of advantages.

Actually, this problem has been unexpectedly solved by the present inventors according to the disclosure hereafter.

SUMMARY OF THE INVENTION

It was surprisingly found that the blood pool agents according to the present invention comprise liposome suspensions which are readily injectable into the circulation of living bodies are sufficiently stable and carry sufficient amount of paramagnetic or X-ray opacifying active material to allow convenient imaging of the blood stream and appended organs. The blood pool agents contain liposomes with astounding so called "stealth" properties without requiring incorporation of the priorly recognised "stealth factors".

The blood pool contrast agents of the invention comprise liposome suspensions in which:

(a) the liposome forming lipids comprise between 80 and 99 mole % of neutral phospholipids and from about 1 to 20 mole % of negatively charged phospholipids, whose phosphatidyl moiety is linked to glycerol, (b) at least 80% (by volume) of the liposome vesicles are in the 0.2–1.0 μm range, and (c) depending on the liposome size the lipid concentration ($C_{Lip}$) in the suspensions is below 20 mg/ml for liposomes with average diameter of 1.0 μm and below 100 mg/ml for liposomes with average diameter of 0.2 μm.

Also disclosed is a method for preparing the blood pool agents by encapsulating a concentrated solution of opacifying agent in the vesicles formed according to liposome making means from a lipid mixture comprising between 80 and 99 mole % of neutral phospholipids and 1 to 20 mole % of negatively charged phospholipids whose phosphatidyl moiety is linked to glycerol, and optionally other additives such as cholesterol, normalising the vesicles by repeated extrusion through calibrated semi-permeable membranes until the size of at least 80% of the vesicles is comprised between 0.2 and 1.0 μm, and optionally, separating the vesicles with the contrast agent entrapped therein from non-encapsulated contrast agent, and adjusting the amount of carrier in the suspension to have a lipid concentration ($C_{Lip}$ in mg/ml) therein not exceeding a value given by the ratio 20/D where D is the vesicle volume average diameter expressed in μm.

Use of the X-ray or NMR blood pool agents in imaging of human or animal patients is also disclosed.

DETAILED DESCRIPTION OF THE INVENTION

The main aspects of the invention are based on the unexpected finding that the liposome suspensions in which (a) the liposome forming lipids comprise between 80 and 99 mole % of neutral phospholipids and from about 1 to 20 mole % of negatively charged phospholipids, whose phosphatidyl moiety is linked to glycerol, (b) at least 80% (by volume) of the liposome vesicles present have the size in the 0.2–1.0 μm range, and (c) depending on the liposome diameter, the maximal lipid concentration ($C_{Lip}$) is between 20 and 100 mg/ml. The maximal concentration (readily calculated as 20/the vesicle average diameter D in μm) means that for liposomes with an average diameter of 0.2 μm the maximal lipid concentration in the suspension is below 100 mg/ml, for liposomes with an average diameter of 0.4 μm the maximal lipid concentration is below 50 mg/ml, for liposomes with an average diameter of 0.6 μm the maximal lipid concentration is below 33 mg/ml, for liposomes with an average diameter of 0.8 μm the maximal lipid concentration is below 25 mg/ml, and for liposomes with an average diameter of 1.0 μm the maximal lipid concentration is below 20 mg/ml. Such suspensions are readily injectable into the circulation of living bodies, they have enough stability to remain in the circulation for prolonged periods of time, they display so called "stealth" properties without requiring incorporation of the recognised "stealth factors" and yet posses sufficient entrapping capacity toward solutions of paramagnetic or X-ray contrast agents to provide very convenient contrast agents useful for imaging the blood stream and appended organs.

It shoud be noted that 1 to 20 mole % of negatively charged saturated or unsaturated phospholipids whose phosphatidyl moiety is linked to glycerol, optionally include phospholipids in which the glycerol is replaced by inositol. The other phosphatidyl moiety of the negatively charged phospholipid is attached to a glycerol diester of the usual fatty acids such as myristic acid, palmitic acid, stearic acid, oleic acid and the like. Addition of more than 20 mole % of the negatively charged phospholipids to the liposomes reduces considerably the entrapment capacity of the vesicles and should thus be avoided. The best results in terms of "stealth" properties and entrapment capacity of the liposomes of the invention are obtained when this range is maintained between 3 to 15 mole %.

In the invention, the neutral phospholipids comprise the usual saturated and unsaturated phosphatidylcholines and ethanolamines, for instance, the corresponding mono- and di-oleoyl-, mono- and di-myristoyl-, mono- and di-palmitoyl-, and mono- and di-stearoyl-compounds. The negatively charged phospholipids comprise the phosphatidyl glycerols preferably dimyristoylphosphatidyl glycerol (DMPG), dipalmitoylphosphatidyl glycerol (DPPG), distearoylphosphatidyl glycerol (DSPG) and optionally the corresponding phospholipids where the glycerol is replaced by inositol. In addition, the lipids of the present liposomes may contain additives commonly present in liposome formulations, like the sterols and some glycolipids; the sterols may include cholesterol, ergosterol, coprostanol, cholesterol esters such as the hemisuccinate (CHS), tocopherol esters and the like. The glycolipids may include cerebrosides, galacto-cerebrosides, glucocerebrosides, sphingo-myelins, sulfatides and sphingo-lipids derivatized with mono-, di- and trihexosides.

It is important to note that the phosphatidic acids must be avoided in the formulations of the present liposome suspensions, as even small amounts thereof will destroy the "stealth" properties. It is also noteworthy that the additional incorporation of the priorly recognised "stealth factors" into the liposomes and the suspensions of the invention (which are useful in other liposome formulations) will bring no further improvement in the "stealth" properties of the present suspensions. The incorporation of these factors into the liposomes will thus have insufficient impact on the residence time of the liposomes of the invention in the blood. Actually, the incorporation of recognised stealth factors to the formulations of the present liposome suspensions may even be detrimental as the captured volume $E_c$ (entrapped volume/weight of lipid) may be significantly reduced. Hence the liposome suspensions of the invention are simple to formulate and manufacture and are thus even economically advantageous in comparison to other formulations of inferior performance.

It is advantageous to use suspensions in which the vesicles have a size distribution as narrow as possible around a nominal value selected in the given 0.2 to 1.0 μm range and preferably in the range between 0.2 and 0.6 μm. For instance, if the selection desirably involves a suspension of vesicles of, say 0.4 μm, it is preferable that at least 80%, according to volume distribution, of the vesicle have a size of 0.4 μm±10%. The narrow width of the vesicle size distribution band can be considered here as a quality factor, i.e. the narrower the band, the more controllable the properties of the liposome suspensions and the better their intrinsic performance as carrier of blood-pool imaging agents in injectable formulations. Narrowing the vesicle size distribution band of liposome suspensions is normally achieved by "normalisation", i.e. calibration of the vesicles by extrusion of the liposome suspensions through accurately graded filtration membranes, for instance Nuclepore® polycarbonate membranes.

From the above it is readily apparent that the admissible lipid concentration ($C_{Lip}$) in the suspensions of the invention is directly related to the vesicle size and its entrapping potential. For instance, at the lower end of the size range, the admitted maximum lipid concentration is 100 mg/ml. This limit corresponds to 0.2 μm vesicles; for 0.6 μm vesicles, this limit is 33 and for 1.0 μm vesicles this limit is 20 mg/ml. These values are preferred although acceptable results may be obtained when the sizes vary within ±20% on the both ends of the limit. These are admissible in view of the property changes which may result from different lipid compositions. Therefore, the viscosity of the present suspensions will not exceed 50 mPa.s and, preferably, it will be below 25 mPa.s. In fact, in some cases, for instance, when exceptionally large injector needles are used or when the injection can be made slow, these values may be overridden.

In the case of X-ray contrast agents the suspensions are prepared from liposomes carrying iodinated compounds, the lipid concentration ($C_{Lip}$) in the suspensions should not be below about a quarter to a half the aforementioned maximal value, as otherwise the amount of opacifying agent carried by the liposomes may become too low for imaging contrast; for instance, for 0.4 μm vesicles, half the maximal value is 25 mg/ml. Hence, with a captured volume ($E_c$) of about 9 μl/mg of lipids (this value which is about ¾ of the theoretical value is easily attainable with liposomes of the present invention) and using for encapsulation, solutions of non-ionic monomers, with the standard iodine solution of concentration $C_I$=260 g of iodine/l (0.26 mg/μl), the final iodine concentration of the liposome suspension ($C_{IS}$) is 25×9× 0.26=58.5 mg/ml, is already above the preferred lower limit of iodine concentration for satisfactory imaging opacification. Of course, the foregoing holds when using iodine solutions of non-ionic monomers with standard 260 g/l concentrations for liposome encapsulation; with solutions of higher iodine concentrations (which for mixtures of monomers and dimers can reach 300 g/l or more) the foregoing relations should be adapted accordingly. However, iodine concentrations much higher than 260 g/l are generally less preferred as osmotic pressure gradient across the vesicle membrane may, in some cases, cause iodine leakage into the outside aqueous carrier medium.

If one considers that the volume of a hollow body relative to its surface varies linearly as a function of its physical size, then, in the case of a sphere of radius "r" (=D/2), the ratio of volume to surface will be r/3. In the case of ideally spherical liposome vesicles bounded by an outer lipid membrane of surface density "φ"(g/cm$^2$), the captured volume ($E_c$) in ml/g (or μl/mg) of lipids is r/3φ. In the lipid bilayer of a unilamellar liposome vesicle, the molecular weight "Mw" of two facing lipid molecules≈2×800, and the area of the corresponding surface element≈50 $Å^2$=5×$10^{-15}$ $cm^2$. Taking the Avogadro's number as 6.02×$10^{23}$, the surface density (φ) of the lipid bilayer=

$$\frac{1600}{6.02 \times 10^{23} \times 5 \times 10^{-15}} \approx 5 \times 10^{-7} \text{ g/cm}^2.$$

For a 100 nm vesicle (diameter D=0.1 μm), the theoretical captured volume ($E_c$=r/3φ) would therefore be approximately $$\frac{50 \times 10^{-7}}{3 \times 5 \times 10^{-7}} \approx 3 \text{ ml/g of lipids (or 3 μl/mg)}.$$

Note that in view of the foregoing $E_c$/D=1/6φ (constant)≈30 when $E_c$ is expressed in μl/mg (or ml/g) of lipids and D in μm. In practice, the vesicles are not perfect, even after careful "size normalisation" e.g. by extrusion. Hence, since the vesicle average size follows a statistical distribution order, the captured volume is usually significantly lower, i.e. it rarely reaches ¼–½ of the calculated value, which means that $E_c$/D may be lower than 10 in the best results reported so far.

As it may be seen in the present invention $E_c$/D values in the order of 10–25 or even more can be reached. Thus until now, even in the best circumstances, the captured volume of a practical 100 nm vesicle available did normally not exceed 2 ml/g (μl/mg) of lipids and were generally much less. Hence, theoretically, if the vesicles are filled with a commonly available concentrated iodine solution (for instance, a 530 g/l solution of iomeprol will provide an iodine concentration ($C_I$) of 260 g/l), the weight of encapsulated iodine available in g per g of lipid (I/L) will be at most 2×0.26=0.52.

Now, as generally admitted in the imaging field, sufficient imaging contrast in the blood-pool advantageously requires an injected dose of at least about 50–100 mg of iodine/kg of body weight and for the safety reasons, this is distributed in an amount of injectable liquid preferably not exceeding 1 ml/kg. Hence, if we wish to distribute (by means of a liposome suspension) 100 mg of iodine in 1 ml of injectable liquid, i.e. to have a concentration ($C_{IS}$) of iodine in the liposome suspension of 100 mg/ml using 100 nm vesicles, we should use a liposome suspension of concentration ($C_{Lip}$)=100/0.52=190 mg of lipids/ml. This value is far too high in terms of viscosity to be considered as useful.

With larger size vesicles, the situation is different. For example, if the foregoing considerations are applied to, say, 1–1.5 μm vesicles, the I/L ratio becomes about 5–6 mg of iodine per mg of lipids (and may even be higher when preparation conditions according to the present invention are used), which means that for having a liposome suspension containing 100 mg of iodine/ml, the lipid concentration can be as low as 15–20 mg/ml. Unfortunately, 1 μm liposome vesicles have a very short life in the blood, even if "stealth" factors are included in the formulations, and furthermore, the viscosity of liposome suspensions involving larger vesicles increases much more rapidly than with smaller vesicles. For instance a 20 mg lipid/ml liposome suspension with mainly 1–1.5 μm vesicles has about the same viscosity [40–50 mPa.s] as a 80–100 mg/ml suspension with 0.2 μm vesicles; and the larger the vesicles, the steeper the viscosity/lipid concentration curve.

It is also of interest to note that the final encapsulated iodine concentration in the liposome suspension, ($C_{IS}$ in mg of iodine/ml), is equal to the iodine concentration ($C_I$ in mg/ml) in the encapsulated solution multiplied by the ratio of the volume of encapsulated liquid to the total volume of the suspension ($C_{EC}$). The latter being equal to the lipid concentration $C_{Lip}$ (in mg/ml) x the captured volume $E_c$ (in ml/mg of lipid). Usually, the captured volume $E_c$, or entrapment capacity, of liposome vesicles is significantly lower than the calculated value, i.e. the $E_c$/D ratio (Ec being in μl/mg and D being in μm) rarely if ever reaches about 15 or more. In the present invention Ec/D may reach 25 or more.

For X-ray opacification, one will preferably encapsulate concentrated solutions of currently available non-ionic organic iodinated opacifiers such as Iopamidol, Iomeprol, Iofratol, Iohexol, Iopentol, Iopromide, Iosimide, Ioversol, Iotrolan, Iotasul, Iodixanol, Iodecimol, 1,3-bis-(N-3,5-bis-[2,3-dihydroxypropylaminocarbonyl]-2,4,6-triiodo-phenyl)-N-hydroxy-acetyl-amino)-propane and mixtures thereof. Solutions of such iodinated compounds currently provide iodine concentrations in the range of 250–300 g/l. As already mentioned, a 530 g/l iomeprol or iopamidol solution corresponds to a $C_I$ of 260 g/l of dissolved iodine thus for 0.4 μm vesicles which, according to the previous discussion, can advantageously capture about 10 μl/mg of lipids (I/L=2.6) or even more, a liposome suspension containing about 40 mg/ml ($C_{Lip}$) of lipids will provide about 2.6×40=104 mg/ml of iodine ($C_{IS}$). This initial iodine concentration ($C_{IS}$) of the injectable suspension is sufficient for good opacification in blood-pool X-ray imaging as, once injected in the bloodstream, it will decrease only slowly with time according to the findings of the invention; one may therefore still operate with liposomes of lower lipid concentrations, i.e. providing entrapped iodine concentrations ($C_{IS}$) of 60–80 mg/ml and even lower if desired. The same kind of considerations will apply to the entrapment of paramagnetic substances intended as contrast agents for NMR imaging. In this case, the paramagnetic substances will be those having also sufficient water solubility to provide efficient contrast enhancement after dilution in the blood stream. Among such substances, one may cite the linear and cyclic alkylene-amine polycarboxylate chelates of NMR responsive transition elements (e.g. the lanthanides) for instance gadolinium-DTPA (Magnevist® of Schering A.G.), gadolinium-BOPTA (of BRACCO), gadolinium-DO3A (Gadoteridol® or ProHance® of BRACCO Diagnostics Inc.), gadolinium-DOTA (Dotarem® of Guerbet), gadolinium-DTPA-BMA (Omniscan® of Salutar), and the like.

It was particularly astounding to find that the liposome vesicles in the suspensions of the present invention can achieve a lifetime in the blood long enough for blood pool imaging and, simultaneously, provide an entrapment capacity adequate to bring to the circulation a quantity of contrast agent sufficient for good image enhancement. Actually, when iodine loaded suspensions of liposomes according to the present invention are used for X-ray imaging the blood-pool of experimental animals, the amount of iodine still in the circulation one hour after injection can be as high as 50% of the injected dose. After 2 hr, the amount can still be about 40% of the injected dose. This property well enables to apply the present suspensions for satisfactorily imaging the blood-pool in most cases. The reasons why this is so, even in the absence of artefacts to prevent the normal physiological elimination of the lipids in the blood and the disappearance of the iodine through the kidneys is still unexplained.

For preparing the present liposome suspensions one can rely on most techniques known in the art for making liposomes and encapsulating substances therein, provided that the suspensions thus obtained are thereafter correctly calibrated by extrusion through conveniently graded filtration membranes, this being to narrow the vesicle size distribution within appropriate limits. The preferred methods involve the hydration of the lipids in an aqueous carrier liquid at or above the lipid transition temperature, either directly in the solution to be encapsulated, or in unloaded aqueous media, this being followed by transmembrane permeation loading (see WO-A-92/10166).

After extrusion, at least 80% by volume of the vesicles should be within the 0.2–1.0 μm and preferably 0.2 and 0.6 μm range. At best, 80% of the vesicles are ±10% from any nominal value selected between 0.2 to 1.0 μm. Any other broader or narrower distribution within the foregoing limits is admissible. After extrusion, the suspension will be checked to ensure that the concentration of lipids in the liposome suspension is adequate, and this may have to be adjusted to be in conformity with the aforediscussed requirements. Adjustment can be effected by dilution with more carrier liquid if the lipid concentration exceeds the aforegiven limits; otherwise, it can be increased by usual means, for instance by micro- or ultra-filtration on membranes of porosities appropriate to retain the vesicles but permeable to the carrier liquid.

Alternatively, the liposome suspensions may be prepared in media without the contrast agent, and thereafter the vesicles filled by incubation in the presence of a concentrated solution of the contrast agent. In this case, the encapsulation will proceed through trans-membrane permeation. Adjustment of the final lipid concentration will then be done as said previously.

The following practical Examples illustrate the invention in more details:

EXAMPLE 1

A solution was prepared containing 59 mg (0.079 mmol) of dipalmitoyl phosphatidyl glycerol sodium salt (DPPG-Na, Mw 744.96; Sygena), 790 mg (1.0 mmol) of distearoyl phosphatidyl choline (DSPC, Sygena), and 193 mg (0.5 mmol) cholesterol (Fluka) in a mixture of 4 ml of methanol and 36 ml of chloroform. The solution was filtered on a sterile filter membrane of 0.2 μm gauge (Macherey Nagel) and a tracer quantity of $^{14}C$-tripalmitin (10 μl in $CHCl_3$; specific activity 50 μCi/ml) was added as marker. The organic solvents were removed by evaporation in a rotary evaporator (Rotavapor) at 40° C. under reduced pressure and the residue was dried overnight at the same temperature under a pressure of 1 Torr.

There was then added to the dry lipids a quantity of iomeprol (BRACCO) solution (530 mg/ml=260 mg of iodine/ml), so that the solution obtained contained approximately ($C_{Lip}$) 15 mg of lipids/ml. Then the solution was heated for about half an hour at 80° C. under gentle stirring to effect hydration of the lipids with consecutive liposome vesicles formation. The liposome suspension was then extruded in succession 5 times through a 2.0 μm polycarbonate filter, then 5 times through a 0.6 μm polycarbonate filter (Nudepore membranes) to effect normalization of the vesicle sizes.

In order to determine the quantity of iodine effectively encapsulated in the liposome vesicles, a 1 ml aliquot of the filtered preparation was dialyzed (dialysis bag from Serva; Mw cutoff≈10.000–15.000) for about 10–12 hrs against 1 l of PBS buffer (Phosphate buffer saline; $PO_4$ 10 mM, NaCl 0.9%). The dialysis operation was repeated once to ensure that all free, non-encapsulated iodine had been removed. To the dialyzed solution (0.9 ml) were added 0.1 ml of a 10% sodium dodecyl sulfate solution and the mixture was heated to 40° C. for 5 minutes. By measuring the optical density of this solution at 260 nm, it was determined at this stage that the final preparation contained 84.41 mg/ml of iomeprol, corresponding to 41.36 mg of iodine per ml. The quantity of lipids effectively present in the preparation was determined by measuring the radioactivity of the sample using a liquid scintillation analyzer (Packard 2200-CA, TRI-CARB®). The lipid concentration (CLip) value found was 14.72 mg/ml, hence the I/L was 2.81.

At this stage, the liposome suspension was microfiltered on an ultrafiltration membrane (Amicon cell) to increase about two times the lipid concentration (to make it about 30 mg/ml).

The mean size of the liposome vesicles and the vesicle size distribution were determined by a Dynamic Light Scattering method (DLS), also known under the name of "Photon Correlation Spectroscopy (PCS) using a Malvern Mastersizer equipment (Malvern Instruments) or a Nicomp 370 HDL-NPSS. The results indicated that the mean size of most vesicles in the present preparation was 0.4 μm with less than 10% above 0.6 μm and under 0.2 μm. Using a particle counter (COULTER Nanosizer), it was found that the mean size of the vesicles was practically 0.4 μm with less than about 20% by weight of the vesicles not within the range of 0.35 to 0.45 μm.

The iodine loaded liposone suspension prepared as above was injected to laboratory rats at the dose of approximately 1 ml/kg of animal (2.81×30=84 mg/kg of animal of encapsulated iodine) and thereafter the animals were subjected to X-ray tomography of the circulation. Satisfactory imaging of the blood vessels was reported including good contrast of left heart portions. The imaging could be pursued for more than about 30 min before fading of the contrast effect became significant.

EXAMPLE 2

Fifty mg of a 9/1 (molar ratio) mixture of distearoylphosphatidyl choline (DSPC) and dipalmitoyl-phosphatidyl-inositol (DPPI) dissolved in 2 ml of a mixture (1/2) of MeOH and $CHCl_3$ were placed in a 5 ml flask and rotoevaporated at 30° C. under 20–30 Torr. There were then added 5.0 ml of distilled water and the mixture was agitated gently for about ½ hr at 60° C. The resulting liposome suspension was then repeatedly extruded at room temperature through a 0.6 μm microporous membrane (polycarbonate).

To the extruded suspension were added 5 ml of a concentrated aqueous iopamidol solution (520 g/L iodine, 1 g/L Tris, and 0.34 g/L EDTA). The mixture was incubated for ½ hr at 60° C., whereby the dissolved iodine penetrated into the liposome vesicles by trans-membrane permeation, and the suspension was allowed to cool. After eliminating as usual (centrifugation or dialysis) the non-entrapped iodine and replacement of the carrier liquid by a buffer equivalent, the average vesicle size and the liposome size distribution were determined by usual means. Values of about 0.56 μm with less than 10% of the vesicles above 0.6 μm and below 0.2 μm were obtained. The I/L measured as disclosed in the previous example was 4.1. This experiment showed that extrusion of the liposomes can also be done before filling the liposome vesicles with iodine.

When injected into laboratory animals after concentrating about 3–4 times by microfiltration, the foregoing preparation enabled satisfactory imaging of the blood vessels by X-ray.

Equally good results were achieved when in place of iopamidol iohexol, ioversol, iopromide or iotrolan were used.

EXAMPLE 3

The following mixture of lipids was dissolved in 20 ml of organic solvent (18 ml of $CHCl_3$ and 2 ml of MEOH):

Distearoylphosphatidyl choline (DSPC) 379.8 mg (63.3 mole %);

Cholesterol 92.5 mg (31.7 mole %);

Dipalmitoylphosphatidyl glycerol Na-salt (DPPG-Na) 28.2 mg (5.0 mole %).

The organic solution was filtered on a 0.2 μm polycarbonate filtration membrane and $^{14}C$-tripalmitin (50 μCi/g of lipid) was added thereto. The solution was then evaporated in a round bottom flask under vacuum in a Rotavapor apparatus (40° C./<1 Torr) for 6 hrs. To the solid residue, there were added 32 ml of a concentrated solution (530 g/l) of iomeprol ($C_I$=260 mgI/l; $C_{Lip}$=15 mg/ml). Hydration, liposome formation and iodine encapsulation were carried out by gentle agitation for 30 min at 80° C.

The liposome suspension was then subjected in succession to a series of extrusions through polycarbonate membranes (Nuclepore®) of various porosity grades, thus leading to four samples (1) to (4), this being according to the following protocol:

TABLE 1

| Number of passes | Pore size (μm) | Sample No |
| --- | --- | --- |
| 5x | 2 | (1), then |
| 5x | 1 | (2), then |
| 5x | 0.6 | (3), then |
| 5x | 0.4 | — |
| 5x | 0.2 | (4) |

The specific activity of the foregoing samples (117087 dpm/mg lipids) was measured by taking an aliquot, admixing with DIMILUME (scintillation liquid) and the radioactivity being measured by means of a BECKMANN LS-8100 scintillation counter.

The vesicle size and size distribution in the foregoing 4 samples was measured using either of the following particle sizing systems: MALVERN Master Sizer and NICOMP Model 370/HPL. The results are presented below. For the samples (2) to (4), the size distribution was such that less than 20% (by volume) of the vesicles were outside the range 0.2 to 0.6 μm. The I/L values were measured using the same technique disclosed in Example 1.

Samples (1) to (4) were tested for their life-time after injection in laboratory animals. For this, they were injected into the caudal vein of Sprague-Dawley rats at the dose of 1 ml/kg of animal. Blood samples were collected at various periods after injection and tested for radioactivity; after

TABLE 2

| Sample | Vesicle size D (μm) | I/L (mg/mg)/ Ec/D (μl.mg$^{-1}$.μm$^{-1}$) |
| --- | --- | --- |
| (1) | 1 | 3.94/15 |
| (2) | 0.6 | 3.44/22 |
| (3) | 0.4 | 2.81/27 |
| (4) | 0.2 | 1.58/30* |

*This value is high and reflects the presence (although less than 20%) of vesicles of size larger than the nominal value.

taking the last blood sample (about 26 hrs after start-up), some of the animals were sacrificed and the blood was gathered in heparinized tubes, as well as the organs, livers, spleens and lungs, which, after having been dried and weighed, were also analyzed as controls. The blood samples were checked as follows: 0.3 ml of blood was admixed with 0.5 ml of a 1:1 "Soluene"-isopropanol solution, then after 1 hr rest, 0.25 ml of $H_2O_2$ (30%) was added, followed by 10 ml of scintillation solution (Hionic Fluor). After another 6 hrs rest in the dark, the radioactivity was measured with a Packard Counter.

In Table 3, there is shown for the samples (1) to (4) the amount of lipid (liposomes) remaining in the blood for various periods of time after injection, this amount being expressed in % of the injected dose.

TABLE 3

| | | Time (hrs) | | |
| --- | --- | --- | --- | --- |
| Sample | 10 min | 1 | 2 | 4 |
| (1) | 63.47 | 23.84 | 9.25 | 2.23 |
| (2) | 76.30 | 41.28 | 23.69 | 9.76 |
| (3) | 71.63 | 48.06 | 36.19 | 23.47 |
| (4) | 78.85 | 56.02 | 44.55 | 33.20 |

Table 4 contains the results obtained by multiplying % of the injected dose, after a certain time "t" in circulation, as given in Table 3, by the startingratio of I/L for the samples presented in Table 2. The results are in

TABLE 4

| | | Time (hrs) | | |
| --- | --- | --- | --- | --- |
| Sample | 10 min | 1 | 2 | 4 |
| (1) | 250.1 | 93.9 | 36.4 | 8.8 |
| (2) | 262.5 | 142.0 | 81.5 | 33.6 |
| (3) | 201.3 | 135.0 | 101.7 | 66.0 |
| (4) | 149.0 | 105.9 | 84.2 | 62.7 | direct proportion to the iodine still present in the blood at time "t".

The results in the foregoing Tables show that the persistance of the vesicles in the blood is in inverse proportion to their size. Thus, for instance, after 1 hr, there is still about 56% of the 0.2 μm vesicles injected initially in the blood, and only 24% of the 1 μm vesicles, however, suspensions containing liposomes with an average size of 1 μm may be used for blood pool imaging provided the imaging is carried out immediately after administration of the suspension to a patient. In some case this may even be desirable as the liposomes of this size have high I/L. It can also be concluded that the 0.6 μm and 0.4 μm vesicles are particularly interesting for imaging as the amount of iodine still in circulation after, say 1 hr, is the most significant. The importance of the contribution of the 0.4 μm vesicles to the persistance of a relatively high level of iodine in circulation is particularly striking after 2 hr. This shows clearly that the formulations according to the invention containing vesicles in the 0.2–0.6 μm range provide an excellent performance regarding effective blood-pool imaging with encapsulated contrast agents, this being without requiring incorporation of sophisticated "stealth" factors.

Figure 1:
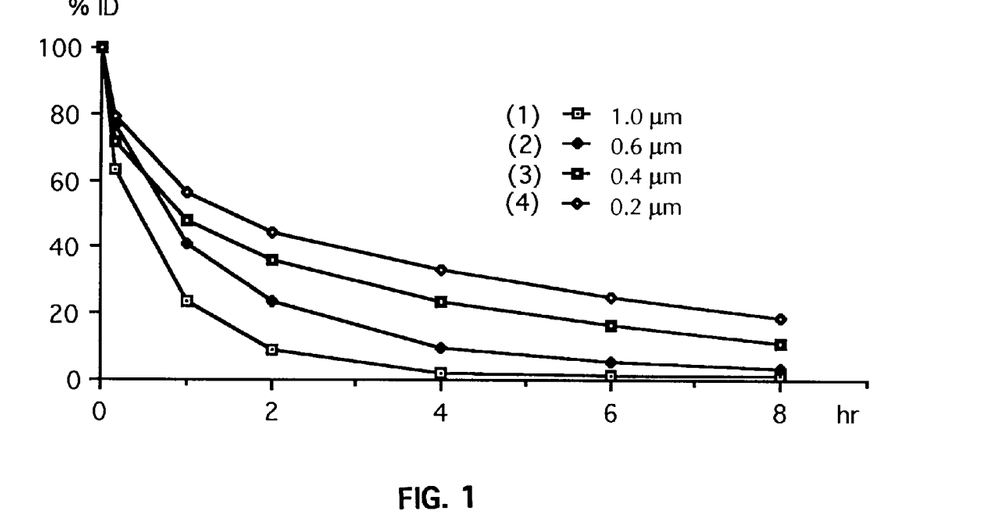
FIG. 1 is a plot of the % of injected dose (ID) as a function of time for the suspensions prepared with liposomes with four different sizes after injection into the bloodstream of laboratory rats.

The graph of annexed FIG. 1 also illustrates the results of this Example by plotting the % of persistance of the initial injected dose versus time for four different vesicle sizes of samples (1) to (4).

EXAMPLE 4

Four liposome suspensions (A to D) calibrated to 0.4 μm vesicle size were prepared according to the directions of Example 3, using the following lipid formulations:

(A) DSPC 340.9 mg (60 mole %); cholesterol 84.0 mg (30 mole %); palmitoylglucuronic acid (PGlcUA) from Nippon Fine Chemicals 30 mg (10 mole %).

(B) DSPC 244.1 mg (60 mole %); cholesterol 59.8 mg (30 mole %); Phosphatidylethanolamine bound to polyethylene glycol of Mw 2000 (PE-PEG) prepared according to T. M Allen et al., Biochim & Biophys. Acta 1066 (1991), 29–36, 147.2 mg (10 mole %).

(C) Formulation identical to that of Example 1.

(D) DSPC (63.3 mole %); cholesterol (31.7 mole %); dipalmitoyl-phosphatidic acid-sodium salt (DPPA-Na) (5 mole %).

The suspensions were subjected to the same checks and analyses as disclosed in the previous Examples, including size distribution (less than 80% of the vesicles outside the range 0.4 µm±10%); and I/L [(A) 0.85, (B) 1.54, (C) 2.81, (D) 2.5]. Note in this connection the adverse effect on the I/L value of the "stealth factors" incorporated to formulations (A) and (B).

The four suspensions were injected into laboratory rats and the blood analyzed periodically as disclosed in Example 3. The results are presented in the graph of annexed FIG. 2 in which the % of the initially injected dose is plotted against time exactly as in FIG. 1.

Figure 2:
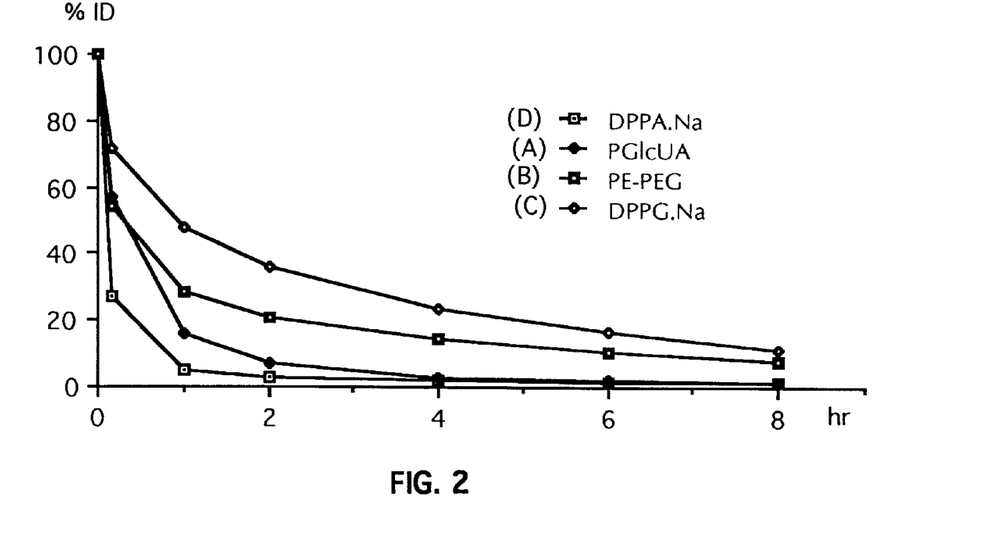
FIG. 2 is a graphical presentation of the % of injected dose (ID) as a function of time for the suspensions prepared with "stealth factors" liposomes and liposomes according to the invention after injection into the bloodstream of laboratory rats.

The results of the graph of FIG. 2 show that the formulation according to the invention (sample C) exhibit longer residence times in the blood than the formulations containing the recognized "stealth factors" PE-PEG and PGlcUA of the prior art (sample A/PGlcUA & sample B/PE-PEG). In addition, not only the formulations prepared with the known "steath factors" have lower residence times in the circulation but the liposomes of these formulations have a lower entrapment capacity.

Therefore, quite contrary to the belief that "stealth" factors are required even when liposomes are very small size (see M. C. WOODLE et al., and I. A. J. M. BAKKER-WOUDENBERG et al., Journal of Drug Targeting 2 (1994) 397–403 and 363–371, respectively) the present results show that this is not necessary provided that the liposomes employed satisfy certain criteria. This unexpected finding is therefore considered as a further proof of the merit of the invention disclosed.

The results also show the negative effect of the presence of DPPA, i.e. a phospholipid with two negative charges on the phosphoryl moiety. It would appear that all liposome formulations containing DPPA are rapidly taken up by the RES.

EXAMPLE 5

Four lipid formulations (E), (F), (G) and (H) given below, were selected and dissolved each with radioactive tracer added in 4 ml of a 1:1 mixture of $CHCl_3$ and methanol:

(E) Hydrogenated soy lecithin (SPC-3) from Lipoid K. G., Germany 71.9 mg (60 mole %); cholesterol 17.8 mg (30 mole %); DPPGNa 11.3 mg (10 mole %).

(F) SPC-3 71.8 mg (60 mole %); cholesterol 17.7 mg (30 mole %); DPPG-Na 8.5 mg (7.5 mole %); DPPA-Na 2.6 mg (2.5 mole %).

(G) SPC-3 (57 mole %); cholesterol (28.5 mole %); DPPA-Na (4.5 mole %); PE-PEG (10 mole %).

(H) Like (G), but the PE-PEG replaced by a mol equivalent of PGlcUA.

The solutions were ridden of the solvents under vacuum and the residues converted to corresponding iodine loaded liposome suspensions (E) to (H) exactly as disclosed in Example 3. Then they were normalized by extrusion, as previously described, to a narrow 0.4 µm size distribution. Analyses for specific activity and I/L were carried out as usual; the I/L values were 2.44 for (E), 2.39 for (F), 1.54 for (G) and 0.81 for (H).

Figure 3:
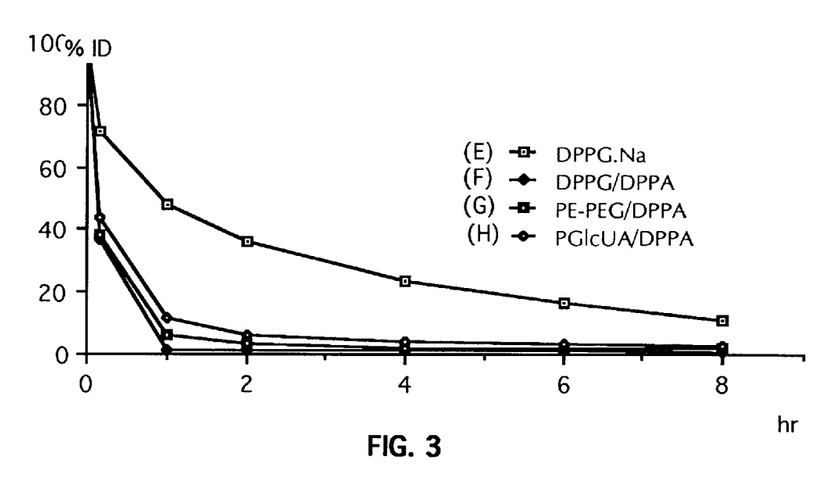
FIG. 3 is a graph of the % of injected dose (ID) as a function of time for the suspensions prepared with liposomes according to the invention and with liposomes containing dipalmitoylphosphatidic acid (DPPA) after injection into the bloodstream of laboratory rats.

The suspensions were tested in rats as disclosed in the previous Examples and the results, plotted as usual in FIG. 3, indicate that (E) was long lasting in the blood as expected. The rapid decay of the formulation (F) demonstrates the dramatic adverse effect of the DPPA on the vesicle stability in the circulation. The curves (G) and (H) show that incorporation of the known "stealth factors" is unable to cure the negative effect of the DPPA. By all means the presence of DPPA or analogues in the liposome suspensions according to the invention should be avoided.

Further experiments were carried out with formulations including less DPPA (down to 1 mole %) and correspondingly more of the aforementioned "stealth" factors PGlcUA and PE-PEG; notwithstanding, the latter were unable to counteract the negative effect of the DPPA. Moreover, it can also be seen from the above I/L results that the conventional "stealth" factors are disadvantageous in the formulations of the present invention as they tend to decrease the capturing capacity of the vesicles (the I/L ratio is low).

If in the previous examples, the DPPG is replaced with an equivalent quantity of diphosphatidyl inositol (DPPI), the liposomes have an equivalent or even longer life in the blood after injection.

EXAMPLE 6

A solution of lipids comprising 152 mg of SPC-3 (63.3 mole %), 37 mg of cholesterol (31.7 mole %), and 11 mg of DPPG.Na (5 mole %) was obtained by dissolving the foregoing ingredients, including a tracer quantity of $^{14}C$-tripalmitin (corresponding to 1310 dpm/mg lipids), in a mixture of methanol (2 ml) and chloroform (18 ml). After removing the volatile solvents with the Rotavapor at 40° C. under about 1 Torr and drying overnight in the same conditions, a dry lipid mixture (~200 mg) remained in the flask. This dry lipid solid was dissolved in a mixture of 20 ml of $CHCl_3$ and 20 ml of diisopropyl ether, and 6 ml of a 0.5 M solution of Gd-BOPTA (BRACCO) were thereafter added. The mixture was heated to 60° C. and subjected to ultrasound (Branson Sonifier) for 3 min; then it was again evaporated under reduced pressure in the Rotavapor (60° C.) to give a residue which was dispersed in 20 ml of PBS. Evaporation was continued until all etheral solvents had been completely removed (odorless residue).

Then the liposome suspension was extruded 5 times through a 2 µm membrane and afterwards five more times through a 1 µm membrane. An aliquot (5 ml) was dialyzed overnight against 2 times 1 l of PBS and subjected to analysis as previously reported. Radioactive counting indicated that the lipid concentration $C_{Lip}$ in the liposome suspension was 5.18 mg/ml; the Gd-BOPTA concentration in the suspension, as determined by HPLC according to J. J. Hagan et al. Anal. Chem. 60 (1988), 514–516 (Fluorescence Detection of Gadolinium Chelates separated by Reverse-phase High-performance Liquid Chromatography), after dissolution of the vesicles by addition of SDS was 8.07 mM, i.e. 1.56 mmol Gd/g of lipids. The average size of the vesicles (Malvern) was 0.52 µm±10%. The dialyzed suspension was thereafter concentrated to about 30 mg lipids/ml using an Amicon ultrafiltration cell.

When injected to laboratory animals, this preparation enabled to provide useful contrast in the MRI imaging of the circulation.

EXAMPLE 7

A solution of lipids was prepared by dissolving 114 mg of SPC-3 (63.3 mole %), 28 mg of cholesterol (31.7 mole %), and 8 mg (5 mole %) of DPPG.Na, including a tracer quantity of 14C tripalmitin (corresponding to 1220 dpm/mg of lipids) in a mixture of MeOH (2 ml) and CHCl$_3$ (8 ml). The solution was subjected to evaporation in a Rotavapor at 40° C. under about 1 Torr to remove the volatile solvents, and it was dried overnight under the same conditions. The dry residue (~150 mg of lipids) was admixed with 10 ml of 0.5 M solution of gadoteridol (ProHance®, BRACCO Diagnostic Inc.) and hydrated by heating at 65° C. for ¾ hr under gentle agitation. This gave a suspension of MLV (multilamellar) liposomes which was thereafter extruded 5 times through a 2 µm polycabonate membrane and then 5 more times through a 0.6 µm membrane. A 5 ml aliquot of the normalized suspension was dialyzed overnight against 2 successive 1 liter portions of PBS and analyzed as before. Radioactive counting indicated a lipid concentration of 6.52 mg/ml. The average size of the liposome vesicles (Malvern) was found to be 0.44 µm±10%. The gadoteridol concentration in the suspension (found 20.67 mM) was determined by HPLC after dissolution of the vesicles in a sample by the addition of SDS; this did correspond to a ratio mmol Gd/g of lipids of 3.17 and to an entrapment capacity Ec of 6.3 µl/mg of lipids (the theoretical entrapment capacity of 0.44 µm vesicles is equal to 13 µl/mg).

The bulk of the suspension was dialyzed as above and thereafter concentrated up to about 40 mg of lipids/ml ($C_{Lip}$) using an Amicon ultrafiltration cell. Upon injection to laboratory animals under the conditions disclosed previously, it enabled to provide useful contrast effects in the MRI of the circulation.

In subsequent experiments the gadoteridol concentration in the suspension after dissolution of the vesicles in a sample as above was found to be 30.18 mM which correspond to a ratio mmol Gd/g of lipids of 4.63 and to an entrapment capacity Ec of 9.2 µl/mg of lipids.

What is claimed is:

1. A method of X-ray imaging of blood pool of human or animal patients comprising the steps of:
   (1) administering intravenously a contrast agent comprising an injectable aqueous suspension of liposome vesicles in a carrier liquid, said vesicles containing encapsulated therein a solution of an iodinated X-ray opacifying compound in which the ratio of the entrapping capacity $E_c$ captured volume of compound in µl/mg of lipid of the vesicles to the size D, where D is the vesicle average diameter in µm thereof, is at least 25, and thereafter
   (2) X-ray imaging the blood pool, wherein
      (a) the liposome forming lipids consist essentially of between 80 and 99% mole of neutral phospholipids and 1% to 20% mole of negatively charged phospholipids selected from the group consisting of dimyristoylphosphatidyl glycerol (DMPG), dipalmitoylphosphatidyl glycerol (DPPG), distearoylphosphatidyl glycerol (DSPG), dimyristoylphosphatidyl inositol (DMPI), dipalmitoylphosphatidyl inositol (DPPI) and distearoylphosphatidyl inositol (DSPI), provided dipalmitoylphosphatidic acid (DPPA) is excluded from the lipids forming the liposomes,
      (b) at least 80% by volume of the liposome vesicles in the suspension are liposomes with size in the 0.2–1.0 µm range,
      (c) the maximal lipid concentration $C_{lip}$ in the suspension is between 20 and 100 mg/ml, and
      (d) the concentration of the iodinated X-ray opacifying compound in the composition available for blood pool imaging is at least 50 g iodine per liter of the injectable aqueous suspension.

2. The method of claim 1 wherein the amount of iodine still in the circulation one hour after injection is about 50% of the injected dose.

3. The method of claim 2 wherein the amount of iodine still in the circulation two hours after injection is about 40% of the injected dose.

4. A method of MRI imaging of blood pool of human or animal patients comprising the steps of:
   (1) administering intravenously a contrast agent comprising an injectable aqueous suspension of liposome vesicles in a carrier liquid, said vesicles containing encapsulated therein a solution of an NMR responsive paramagnetic substance in which the ratio of the entrapping capacity $E_c$ captured volume of substance in µl/mg of lipid of the vesicles to the size D, where D is the vesicle average diameter in µm thereof, is at least 25, and thereafter
   (2) MRI imaging the blood pool, wherein
      (a) the liposome forming lipids consist essentially of between 80 and 99% mole of neutral phospholipids and 1% to 20% mole of negatively charged phospholipids selected from the group consisting of dimyristoylphosphatidyl glycerol (DMPG), dipalmitoylphosphatidyl glycerol (DPPG), distearoylphosphatidyl glycerol (DSPG), dimyristoylphosphatidyl inositol (DMPI), dipalmitoylphosphatidyl inositol (DPPI) and distearoylphosphatidyl inositol (DSPI), provided dipalmitoylphosphatidic acid (DPPA) is excluded from the lipids forming the liposomes,
      (b) at least 80% by volume of the liposome vesicles in the suspension are liposomes with size in the 0.2–1.0 µm range, and,
      (c) the maximal lipid concentration $C_{lip}$ in the suspension is between 20 and 100 mg/ml.

5. The method according to claim 1 or 4, wherein for liposomes with an average diameter of 0.2 µm the maximal lipid concentration is between 20 and 100 mg/ml.

6. The method according to claim 1 or 4, wherein for liposomes with an average diameter of 0.4 µm the maximal lipid concentration is between 20 and 50 mg/ml.

7. The method according to claim 1 or 4, wherein and for liposomes with an average diameter of 0.6 µm the maximal lipid concentration is between 20 and 33 mg/ml.

8. The method according to claim 1 or 4, wherein for liposomes with an average diameter of 0.8 µm the maximal lipid concentration is between 20 and 25 mg/ml.

9. The method according to claim 1 or 4, wherein for liposomes with an average diameter of 1.0 µm the maximal lipid concentration is 20 mg/ml.

10. The method according to claim 1 or 4, in which the size of at least 80% by volume of the liposome vesicles in the suspension is in the 0.2–0.6 µm range.

11. The method according to claim 1 or 4, in which the negatively charged phospholipids are present in an amount of 3% to 15 mole %.

12. The method according to claim 1 or 4, in which the negatively charged phospholipid is distearoylphosphatidyl glycerol (DSPG) or distearoylphosphatidyl inositol (DSPI).

13. The method according to claim 1 or 4, in which viscosity is below 50 mPa.s.

14. The method according to claim 1 or 4, in which viscosity is below 25 mPa.s.

15. The method according to claim 1 or 4, in which the neutral phospholipids are selected from the group consisting of the hydrogenated soya lecithins, dimytistoylphosphati dylcholine (DMPC), dipalmitoyl-phosphatidylcholine (DPPC) and distearoylphosphatidylcholine (DSPC).

16. The method according to claim 1, in which the X-ray opacifying compound is selected from the group consisting of Iopamidol, Iomeprol, Iohexol, Iopentol, Iopromide, Iosimide, Ioversol, Iotrolan, Iotasul, Iodixanol, Iodecimol, 1,3-bis-(N-3,5-bis-[2,3-dihydroxy-propylaminocarbonyl]-2, 4,6-triiodo-phenyl)-N-hydroxy-acetyl-amino)-propane and mixtures thereof.

17. The method according to claim 16, in which the concentration of the iodinated opacifying compound available for blood-pool imaging is between 50 and 120 g iodine/l.

18. The method according to claim 4, in which the paramagnetic substances are selected from Gd-DTPA, Gd-BOPTA, Gd-DTPA-BMA, Gd-DOTA, and Gd-DO3A.

* * * * *